US009628954B2

(12) United States Patent
Bai et al.

(10) Patent No.: US 9,628,954 B2
(45) Date of Patent: *Apr. 18, 2017

(54) DATA ANALYSIS SYSTEM WITH MOVEMENT PATTERNS FOR MEDICAL WELLNESS CORRELATION

(71) Applicant: International Business Machines Corporation, Armonk, NY (US)

(72) Inventors: Kun Bai, Hartsdale, NY (US); Jenny S. Li, Danbury, CT (US); Ming Li, Elmsford, NY (US); Fei Wang, Ossining, NY (US); Liangzhao Zeng, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,584

(22) Filed: Sep. 14, 2015

(65) Prior Publication Data

US 2016/0381507 A1 Dec. 29, 2016

Related U.S. Application Data

(63) Continuation of application No. 14/753,854, filed on Jun. 29, 2015.

(51) Int. Cl.
*H04W 4/02* (2009.01)
*H04W 4/14* (2009.01)
*G06F 19/00* (2011.01)

(52) U.S. Cl.
CPC .......... *H04W 4/023* (2013.01); *H04W 4/028* (2013.01); *H04W 4/14* (2013.01); *G06F 19/30* (2013.01)

(58) Field of Classification Search
None
See application file for complete search history.

(56) References Cited

U.S. PATENT DOCUMENTS

| 2010/0169220 A1* | 7/2010 | Choing | G06Q 40/08 705/51 |
| 2014/0114677 A1* | 4/2014 | Holmes | G06F 19/345 705/2 |

OTHER PUBLICATIONS

List of IBM Patents or Patent Applications Treated as Related; (Appendix P), Filed Jun. 29, 2015, 2 pages.
Kun Bai et al., "Data Analysis System with Movement Patterns for Medical Wellness Correlation", U.S. Appl. No. 14/753,854, filed Jun. 29, 2015.

\* cited by examiner

*Primary Examiner* — Daniel Lai
(74) *Attorney, Agent, or Firm* — Cantor Colburn LLP; William A. Kinnaman, Jr.

(57) ABSTRACT

A computer program product comprising a tangible storage medium readable by a processing circuit and storing instructions for execution by the processing circuit for implementing a data analysis method is provided. The data analysis method includes generating first data identifying traversed cellular areas and time spent by a mobile device in each, wherein the mobile device is disposable to be carried by a user from first to second locations and to thereby traverse the cellular areas, generating second data identifying the first and second locations as well as time spent by the mobile device in each and performing, by a processor for output to a wellness professional, a wellness analysis of a user based on medical data and the first and second data.

4 Claims, 7 Drawing Sheets

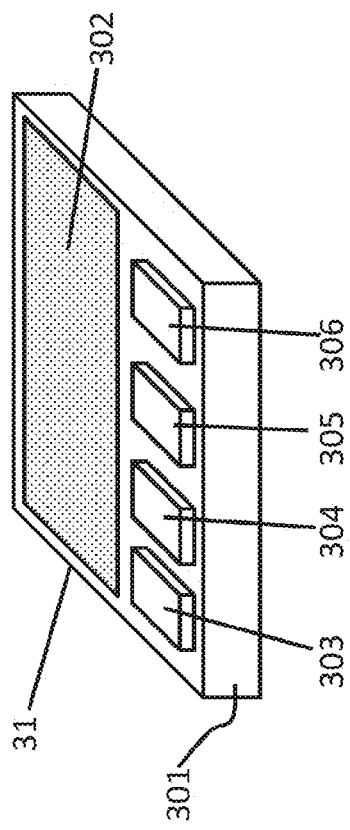
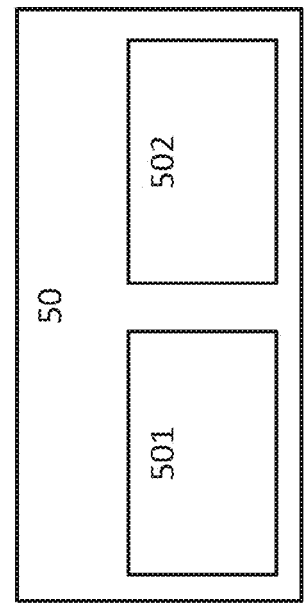
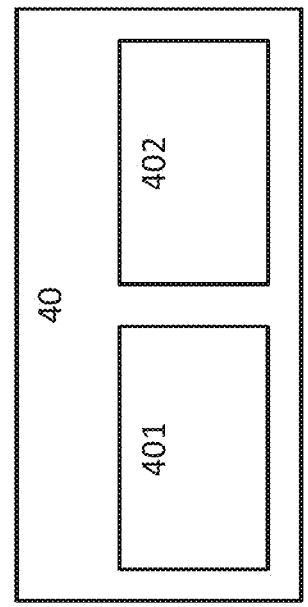

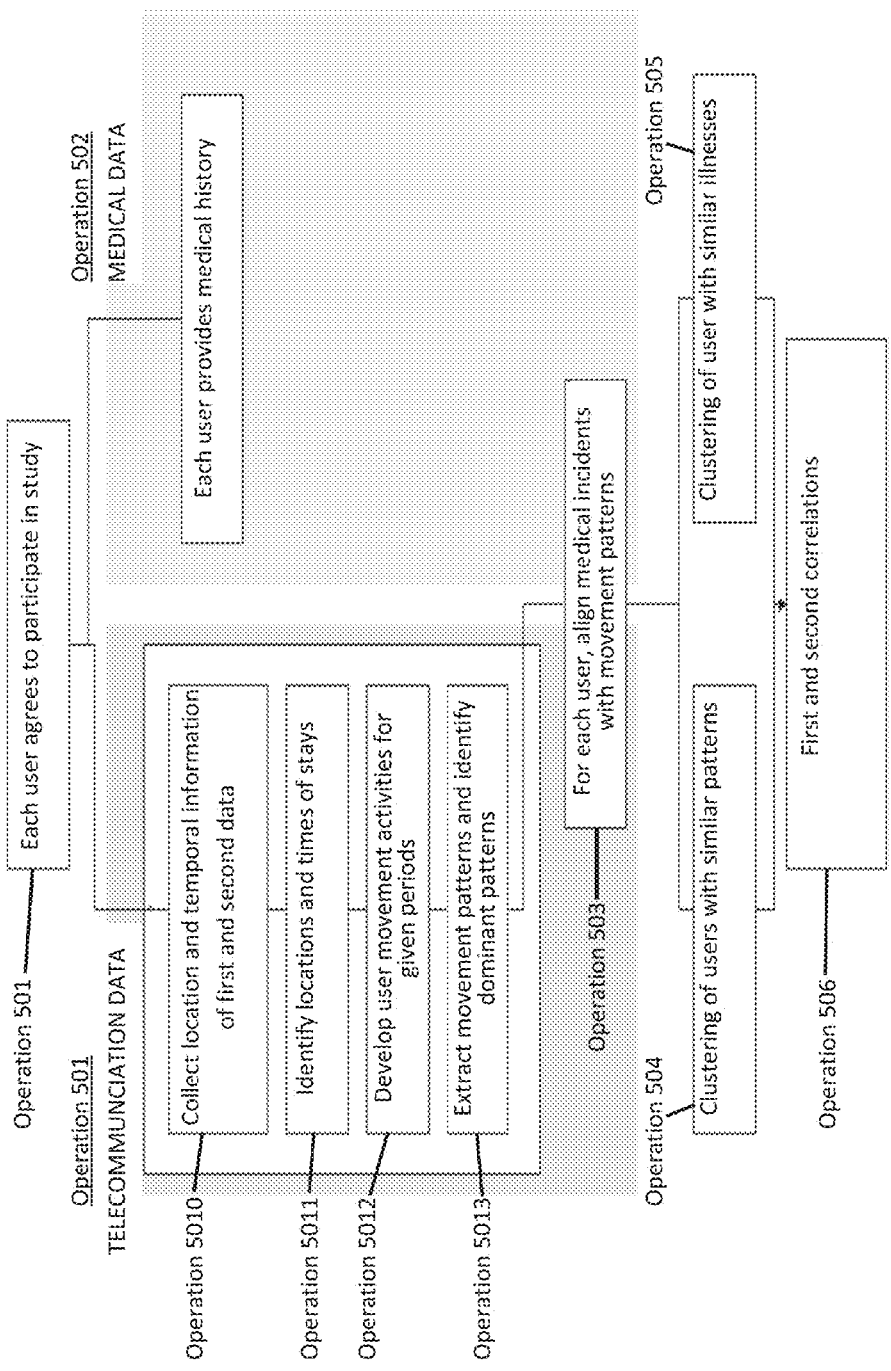

DATA ANALYSIS SYSTEM WITH MOVEMENT PATTERNS FOR MEDICAL WELLNESS CORRELATION

DOMESTIC PRIORITY

This application is a continuation of U.S. application Ser. No. 14/753,854, which was filed Jun. 29, 2015. The entire disclosures of U.S. application Ser. No. 14/753,854 are incorporated herein by reference.

BACKGROUND

The present invention relates to a data analysis system and, more specifically, to a system for data analysis with movement patterns for medical wellness correlation.

Doctors retain medical histories of their patients. These medical histories mostly record what symptoms or sicknesses the patients had over time but generally lack information about their patients' daily activities. On the other hand, telecommunication providers can access users' whereabouts by tracking their phone locations and thus have the capability of generating information about the users' daily activities.

Even if the medical histories and the daily activity information is generated and maintained in good order, the medical histories will be stored in one location and the daily activity information will be stored in another. That is, telecommunication data and medical data will at best be retained by various entities in various industries with little to no sharing. Indeed, doctors do not have access to their patients' whereabouts on a daily basis and telecommunication providers certainly do not have access to users' medical histories.

SUMMARY

According to one embodiment of the present invention, a computer program product comprising a tangible storage medium readable by a processing circuit and storing instructions for execution by the processing circuit for implementing a data analysis method is provided. The data analysis method includes generating first data identifying traversed cellular areas and time spent by a mobile device in each, wherein the mobile device is disposable to be carried by a user from first to second locations and to thereby traverse the cellular areas, generating second data identifying the first and second locations as well as time spent by the mobile device in each and performing, by a processor for output to a wellness professional, a wellness analysis of a user based on medical data and the first and second data.

According to another embodiment of the present invention a mobile device disposable to be carried by a user from first to second locations and to thereby traverse cellular areas is provided and includes a networking unit, a processing unit and a storage unit having medical data and executable instructions stored thereon. When executed, the executable instructions cause the processing unit to execute a method including generating first data identifying traversed cellular areas and time spent by the mobile device in each, generating second data identifying the first and second locations as well as time spent by the mobile device in each and performing a wellness analysis of the user based on the medical data and the first and second data.

According to another embodiment of the present invention, a data analysis system is provided and includes a mobile device disposable to be carried by a user from first to second locations and to thereby traverse cellular areas. The mobile device is configured to generate first data identifying traversed cellular areas and time spent by the mobile device in each, and the mobile device is configured to generate second data identifying the first and second locations as well as time spent by the mobile device in each. The data analysis system further includes a processing apparatus receptive of the first and second data and configured to perform a wellness analysis of at least the first and second data.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 2 is a schematic diagram illustrating components of a mobile device and a central computing device or server in accordance with embodiments;

FIG. 3 is a schematic illustration of a packet of time-stamped location and temporal first data;

FIG. 4 is a schematic illustration of a packet of time-stamped location and temporal second data;

FIG. 5 is a flow diagram illustrating a system process in accordance with embodiments;

DETAILED DESCRIPTION

As will be described below, a person's wellness status may be related to his daily activities. For example, an active person may generally be healthier than a sedentary person and thus the person's movement pattern can be an indicator for his wellness status and therefore it is important to understanding the person's movement pattern when managing his wellness. Traditionally, dedicated devices have been required to monitor people's movement patterns, which required extra infrastructure to be deployed and presented inconveniences for some users. With the prevalence of portable computing (e.g., smartphones, tablets and fit bits), however, dedicated monitoring devices are no longer needed and gaps between the storage of telecommunication and medical data can be filled. As such, information about a person's daily activities can be gathered in a non-intrusive way and be shared with his doctors.

To this end, a system is proposed that utilizes existing mobile devices and network infrastructure to retrieve location data on which data analysis is performed to extract a person's movement pattern. Further, by understanding the similarity of the movement pattern with other people's movement patterns, the system can provide insight of wellness status to doctors. In some cases, the system can be used as a component of medical studies where volunteers allow their location data to be gathered and shared with their doctors or as a service provided by doctors or insurance companies. The location data is gathered non-intrusively by way of cell tower location estimation (that does not require a GPS feature) and analyzed based on location information and time of each data point. As a result of this analysis, the system can estimate a time of stay per location, create a weighted record of daily movement activities and identify movement patterns.

Once the movement patterns are identified, multiple additional tiers of big data analysis can be performed. At tier 1, a person's illness can be correlated with his movement patterns. At tier 2, a group that share similar illness can be correlated with similar movement patterns. At tier 3, a group with similar movement patterns can be correlated with a dominant illness.

Figure 1:
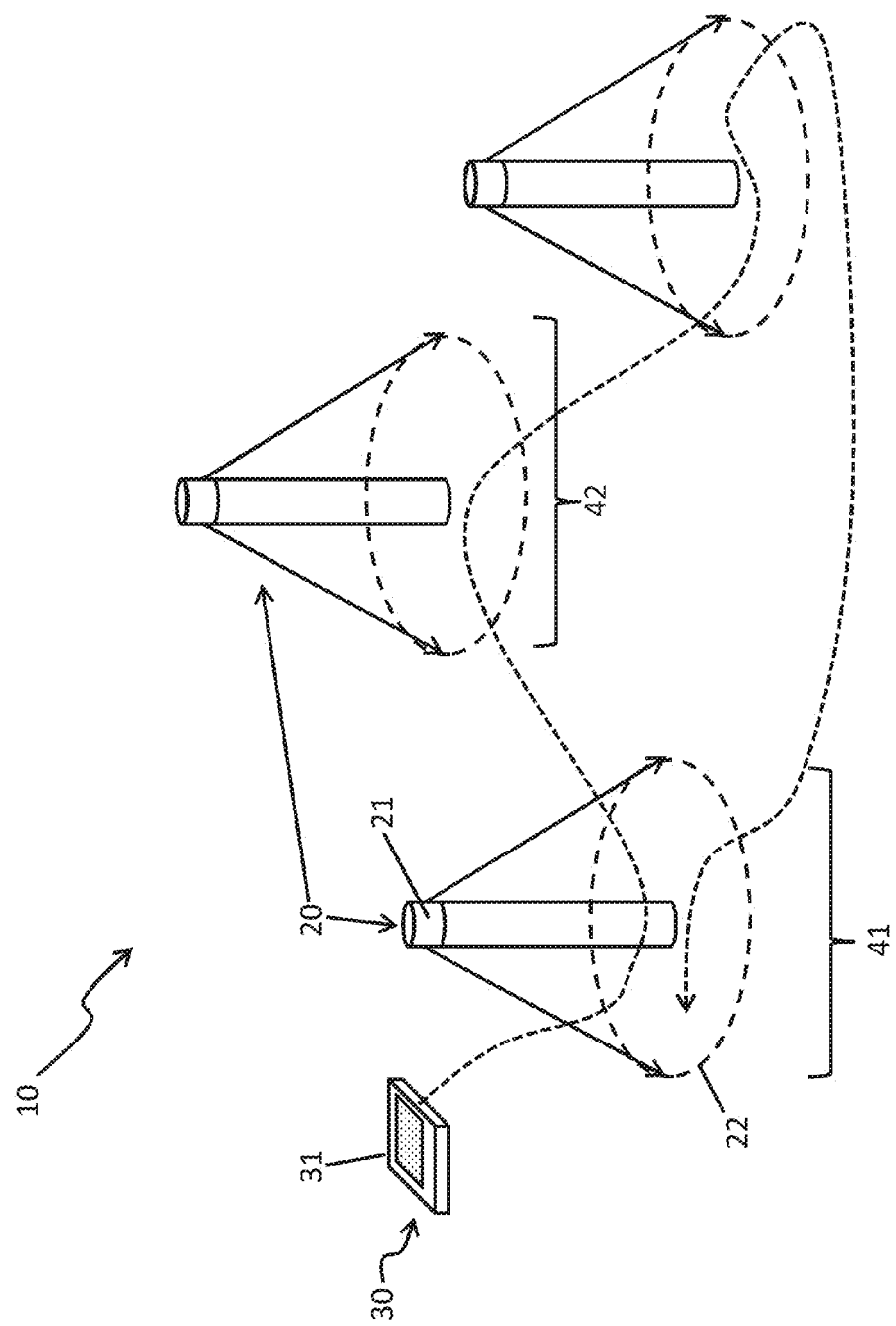
FIG. 1 is a schematic diagram illustration a data analysis system in accordance with embodiments.

With reference to FIG. 1, a data analysis system 10 is provided and includes towers 20 and at least one mobile device 30. The towers 20 may be provided as cellular or cell phone towers and each include broadcasting elements 21. The broadcasting elements 21 are each configured to send out a signal that defines a cellular area 22 in the vicinity of the broadcasting element 21. This signal enables cell phone communication by way of the broadcasting element 21 for any cell phone in the cellular area 22. For those cell phones that are being carried from one cellular area 22 to another, the cell phone communication is carried by way of the broadcasting element 21 of the first cellular area 22 the cell phone occupies and is switched over to the broadcasting element 21 of the cellular area 22 the cell phone enters.

The at least one mobile device 30 may be provided as a mobile computing device, such as a smartphone 31, a tablet, a laptop or computerized fitness apparel. The at least one mobile device 30 is thus disposable to be carried by a user from any one or more first locations 41 to any one or more second locations 42 and so on. In so doing, the at least one mobile device 30 traverses cellular areas 22 defined between the one or more first locations 41 and the one or more second locations 42. In any case, with reference to FIG. 2, each mobile device 30 may include a housing 301 with a display unit 302 and a networking unit 303 disposable in signal communication with the towers 20 and, in some cases, with a central computing device or server.

Each mobile device 30 may further include a processing apparatus. The processing apparatus includes a processing circuit or unit 304, a tangle storage medium or unit 305 and a secured data unit 306. Similarly, as shown in FIG. 1, the central computing device or server may further include processing apparatus that encompasses a processing unit, a storage unit and a secured data unit.

The storage unit 305 of the mobile device 30 has medical history data of the user stored thereon and may have medical history data of other users stored thereon as well. The storage unit 305 may also have executable instructions stored thereon, which, when executed, cause the processing unit 304 to store first and second data (to be described below) in the storage unit 305 by way of the networking unit 303 and to conduct a wellness analysis as described herein. This wellness analysis is conducted in accordance with the medical history data of at least the user and the stored first and second data as well as the medical history data of the other users where the same is available.

The processing unit and the storage unit of the central computing device or server may be configured in a similar manner as the processing unit 304 and the storage unit 305 of the mobile device 30. As such, the storage unit of the central computing device or server may also have executable instructions stored thereon, which, when executed, cause the processing unit to receive first and second data (to be described below), to store the first and second data in the storage unit and to conduct a wellness analysis. As above, this wellness analysis is conducted in accordance with the medical history data of at least the user and the stored first and second data as well as the medical history data of the other users.

With reference to FIG. 3, the first data includes location and temporal data 40 and may be generated by any one or more of the towers 20 and the at least one mobile device 30 (hereinafter referred to in the singular) for local or remote transmission to either or both of the processing apparatuses. The location component of the first data 40 includes location information 401 that identifies cellular areas 22 that have been traversed by the mobile device 30. In accordance with embodiments, the location information 401 may be derived from Global Positioning System (GPS) information or some other suitable source. The temporal component of the first data 40 includes temporal information 402 that is reflective of time spent by the mobile device 30 in each of the cellular areas 22. In accordance with embodiments, the temporal information 402 may include a time-stamp associated with each discrete entry and exit of the mobile device 30 relative to a given one of the cellular areas 22.

With reference to FIG. 4, the second data includes location and temporal data 50 and may be generated by the mobile device 30 for local or remote transmission to either or both of the processing apparatuses. While the first data is generated when the mobile device 30 enters and exits the cellular areas 22, the second data is generated when the mobile device 30 executes an action. Such execution of an action may include, but is not limited to, time-stamped beacon signaling whereby the processing apparatus issues a time-stamped beacon signal by way of the networking unit 303 after a predefined time of non-activity, time-stamped cellular telephone service, time-stamped short messaging service (SMS) and time-stamped email service.

For each action executed, the location component of the second data 50 includes location information 501 that identifies the cellular areas 22 in which the action was executed. In accordance with embodiments and, as noted above, the location information 501 may be derived from Global Positioning System (GPS) information or some other suitable source. The temporal location component of the first data includes temporal information 502 that is reflective of the time the mobile device 30 executed the action. In accordance with embodiments and, as noted above, the temporal information 502 may include a time-stamp associated with each discrete action.

In accordance with embodiments and, with reference to FIG. 5, the wellness analysis will now be described as a component of an exemplary overall wellness analysis system process. As shown in FIG. 5, the system process is initiated when the user (along with other users) agrees to participate in a medical or wellness study (operation 500). In doing so, the user(s) may, for example, permit installation of corresponding applications onto his mobile device 30 or another one of his mobile computing devices synced to his mobile device 30. Next, telecommunication data (e.g., the first and second data described above) and the user(s)' medical data are stored in parallel (operations 501 and 502, respectively). The storage location may be local or remote with respect to the mobile device 30 but will, in any case, be at least partially accessible by way of each of the processing apparatuses. That is, the user may be able to access his own telecommunication data, his own medical history and only selected items from other users' medical histories by way of the mobile device 30. By contrast, a doctor or central administrator may have access granted by the secured data unit 306, 326 to each user's telecommunication data and entire medical history.

Within operation 501, the location information 401 and 501 of the first and second data and the temporal information 402 and 502 of the first and second data are collected (operation 5010) and various locations where the user traveled to and his time of stay there are identified and determined (operation 5011). Next, movement patterns of the user for a defined period of time are developed in accordance with the results of operation 5011 (operation 5012) and these movement patterns are extracted so that dominant patterns can be identified (5013).

Following the parallel operations 501 and 502, the system process continues by aligning medical incidents with specific movement patterns for each user (operation 503). Then, in further parallel operations, users with similar movement patterns are clustered (operation 504) and user with similar illnesses are clustered (operation 505). Following the further parallel operations 504 and 505, additional analytics generates first correlations of the user and the other users sharing similar medical data with similar movement patterns and second correlations of the user and the other users sharing similar movement patterns with similar medical data (operation 506).

With reference to FIGS. 6-9, an exemplary implementation of the data analysis system 10 and the system processes of FIG. 5 will now be described.

Figure 6:
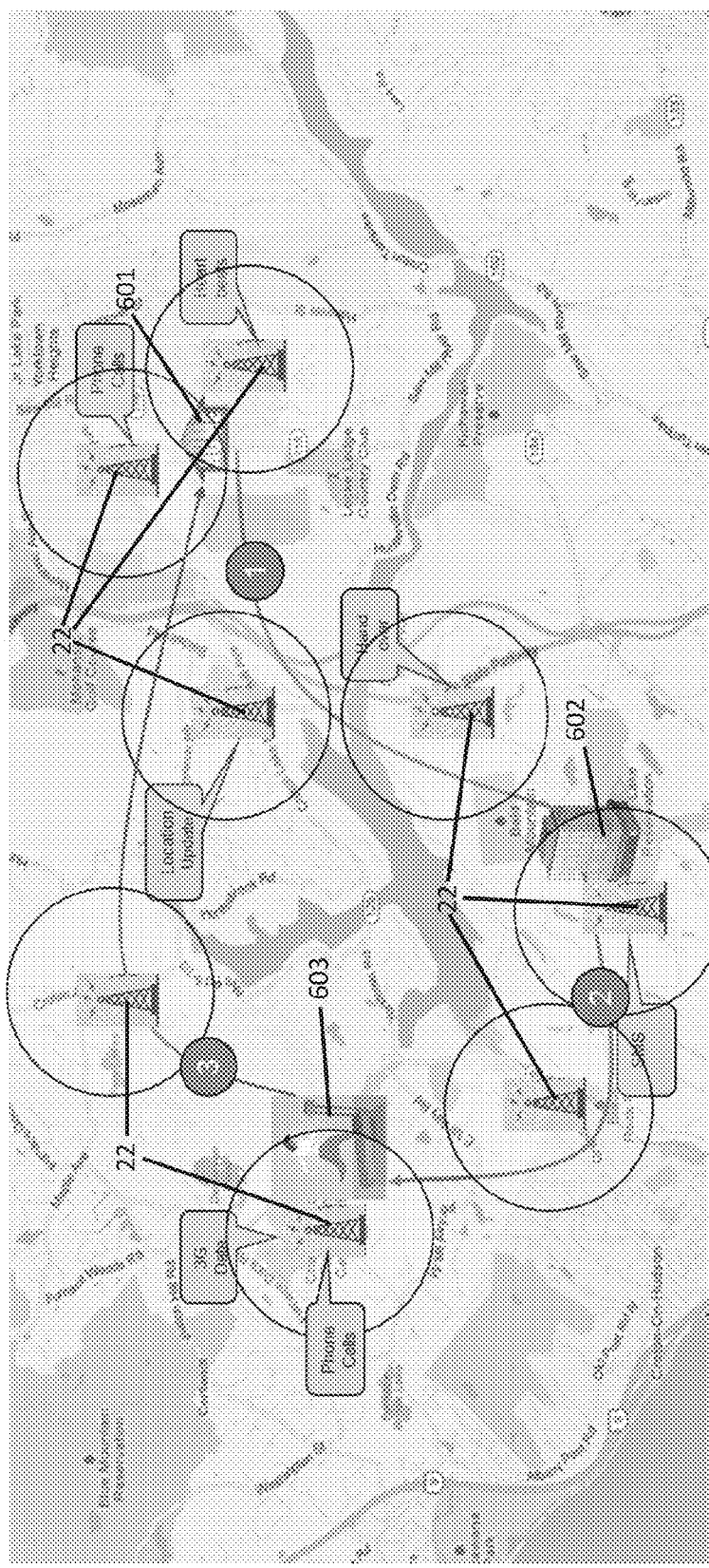
FIG. 6 is a flow diagram illustrating a movement pattern of a user in accordance with embodiments.

As shown in FIG. 6, a user stayed at home 601 at night and made a few phone calls with his smartphone (i.e., mobile device 30), which, during periods of little to no action, exchanged beacon signals with a nearby tower 22. In the morning, the user traveled from home 601 to work 602 and, on his way, he switched from one cellular area 22 to another, which triggered multiple cellular area 22 change signals. When he arrived at work 602, he made phone calls and sent SMS. The user then left work 602 to go to the gym 603 in the afternoon and again switched from one cellular area to another. At the gym 603, the user listened to online radio using his phone, which triggered a 3G data signal. At the end of the day, the user drove back home 601 and switched back into the original cellular area 22.

Figure 7:
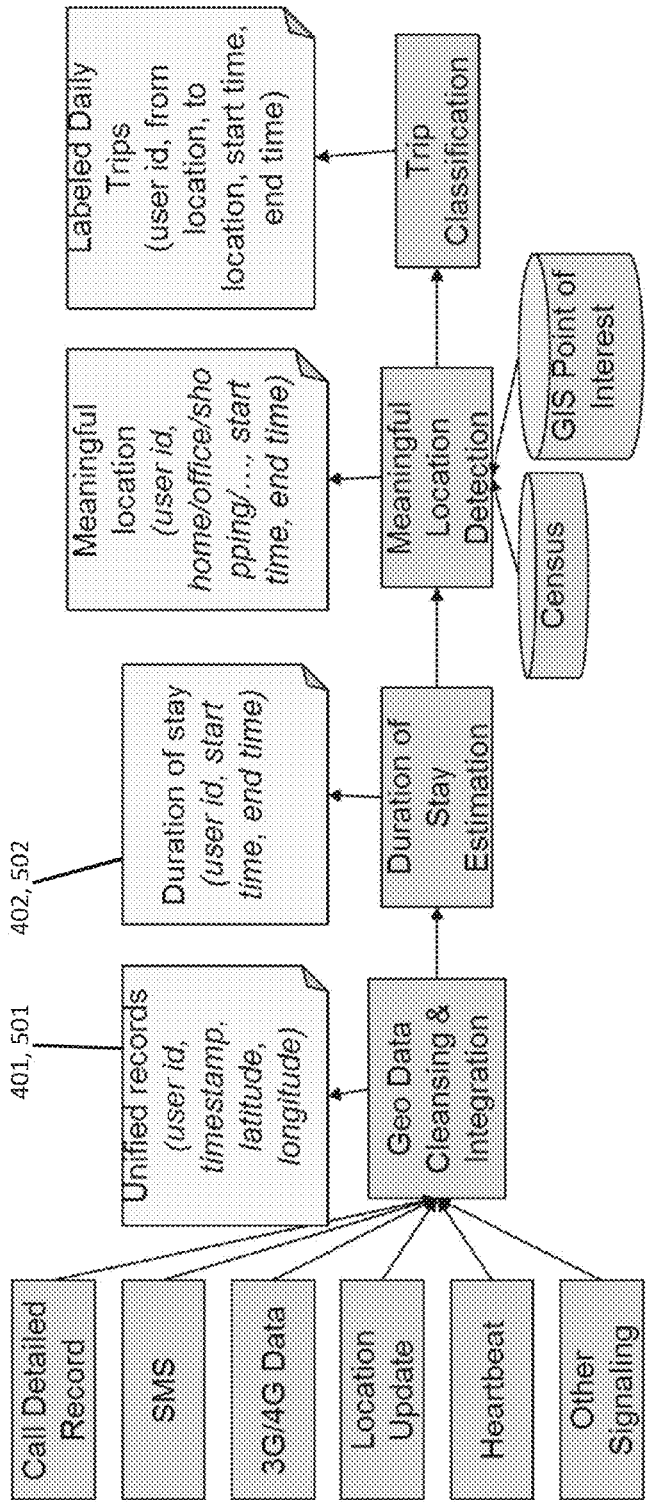
FIG. 7 is a schematic diagram illustrating a processing map of a mobile device of the user of FIG. 6.

As shown in FIG. 7, each time the user's smartphone entered and exited a cellular area 22, location information 401 and temporal information 402 of first data was generated. Similarly, each beacon signal exchange with a tower 22, phone call, SMS exchange, email and online radio activation lead to generation of location information 501 and temporal information 502 of second data.

Figure 8:
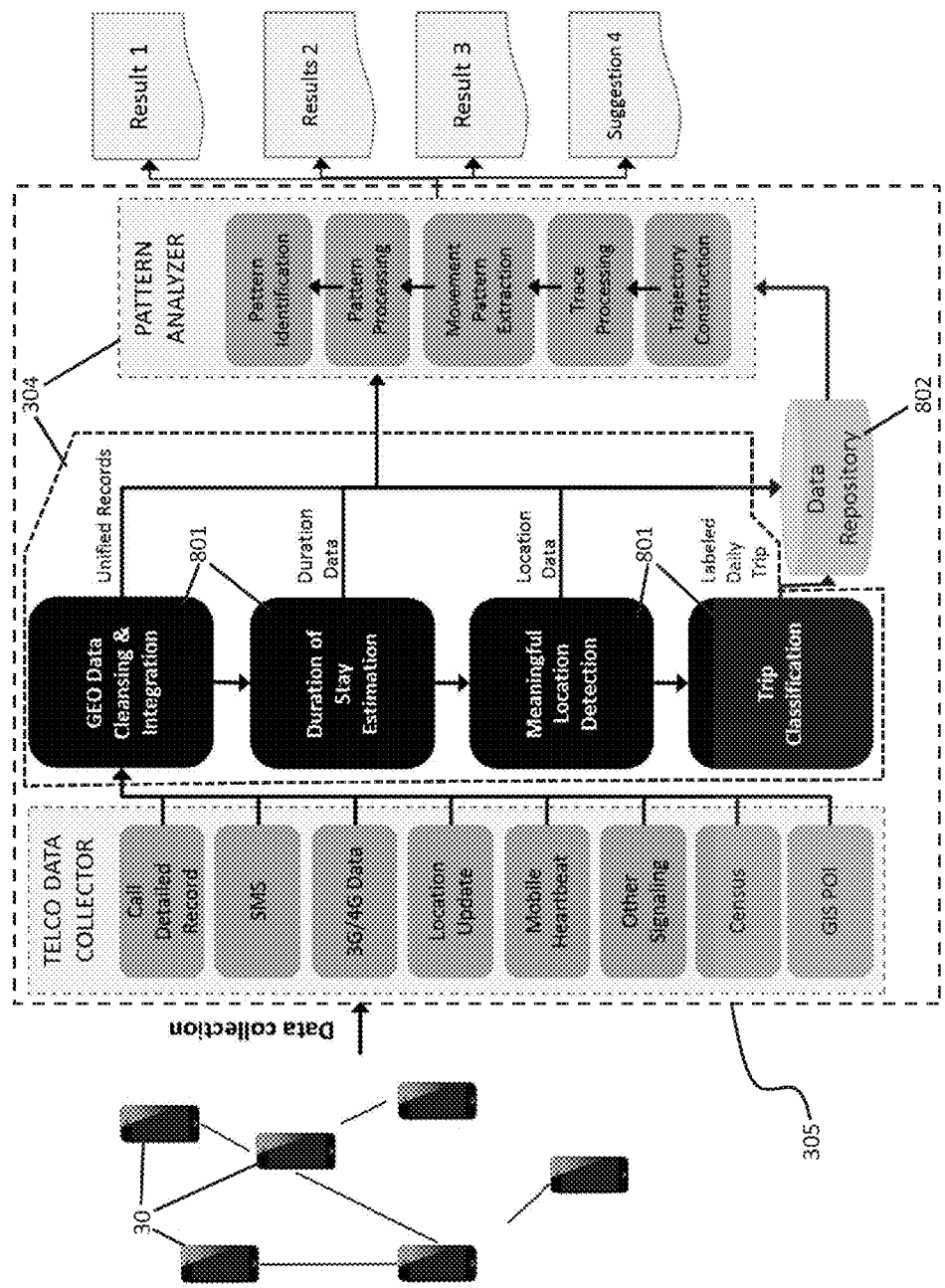
FIG. 8 is a schematic diagram illustrating a further processing map of multiple mobile devices of multiple users.

As shown in FIG. 8, call detailed records, SMS exchanges, 3G/4G data access, location updates, beacon signal (i.e., heartbeats) exchanges with towers 22 and other signals for each user and each of the users' mobile devices 30, are collected and used to generate multiple data items 801 by, e.g., the processing unit 304 of the mobile device 30, the processing unit of any other mobile device or the processing unit of the central computing device or server. The multiple data items 801 include, but are not limited to, cleaned and integrated geographic data describing where each user has been over a given period of time, duration-of-stay data describing how long each user stays in each location, meaning location detection describing which locations are most often visited for the longest times and trip classification data describing the type of visits each user exhibits at each meaningful location.

The multiple data items 801 are then stored in a data repository 802, which may be embodied as portion of the storage unit 305 of the mobile device 30, as a portion of the storage unit of any other mobile device or as a portion of the storage unit of the central computing device or server. The data repository 802 is accessible by one or more of the mobile devices 30 via the presentation of appropriate access rights so that the wellness analysis described above with respect to FIG. 5 can be performed.

Figure 9:
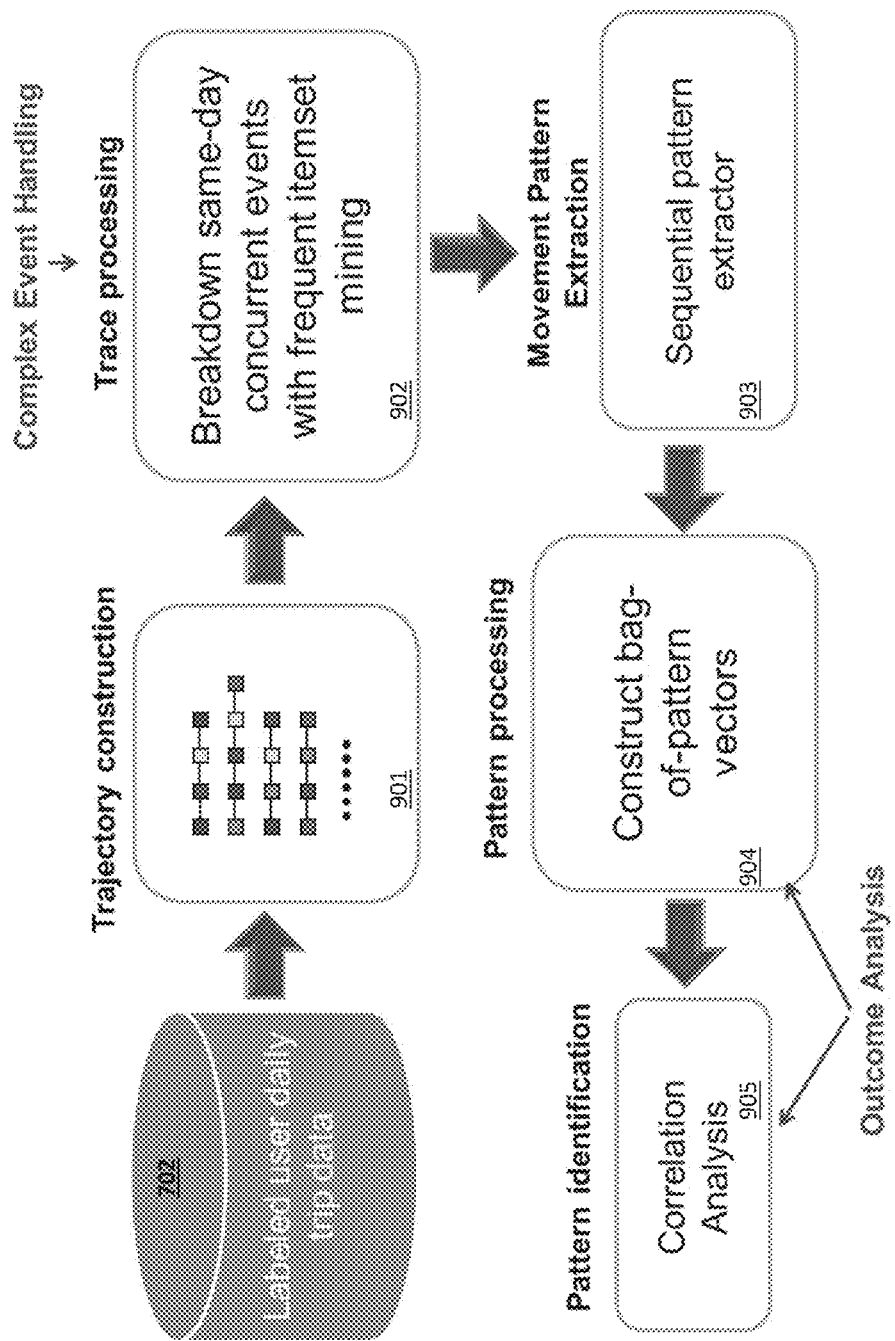
FIG. 9 is a schematic diagram illustrating a final processing map of multiple mobile devices of multiple users.

In accordance with embodiments and, as shown in FIG. 9, the wellness analysis is performed on the multiple data items in the data repository 802 by generating trajectory construction data based on at least the trip classification data 901. Next, complex event handling leads to trace processing by way of a breakdown of same-day concurrent events with frequent item set mining 902. Once the trace processing is completed, a movement pattern extractor 903 extracts the movement patterns of each of the users, which are then processed to construct a set of bag-of-pattern vectors 904. These vectors are then employed in outcome analysis seeking to identify patterns in the vectors for correlation analyses 905.

Thus, as an example, the system might be able to identify users whose movement patterns indicate a greater affinity for going to the gym and staying at the gym longer. However, if the medical histories of those users indicate that some experience particularly high injury rates to a similar body part while others have no such injuries, the system would be able to identify a potential cause of the injury and a medical professional using the system could recommend alternate strategies for recuperation or maintaining fitness instead of going to the same gym.

By contrast, the system might be able to identify users whose movement patterns indicate frequent visits to fast food restaurants while the medical histories of those users indicate that only some experience particularly high blood pressure or heart disease while others have no such problems. In this case, the system would be able to identify a potential cause of the high blood pressure and heart disease for those users while also indicating that fast food does not seem to affect the other users as badly. A medical professional using the system could then recommend avoiding fast food for the affected users but might not feel the need to make the same type of recommendation for the unaffected users.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A computer program product comprising a non-transitory storage medium readable by a processing circuit and storing instructions for execution by the processing circuit for implementing a data analysis method, comprising:

generating first data identifying traversed cellular areas and time spent by a mobile device in each, wherein the mobile device is disposable to be carried by a user from first to second locations and to thereby traverse the cellular areas;

generating second data identifying the first and second locations as well as time spent by the mobile device in each;

performing, by a processor and for output to a wellness professional, a wellness analysis of a user based on medical data and the first and second data;

establishing access rights to a result of the wellness analysis; and displaying the results of the wellness analysis to a user holding the established access rights, wherein the wellness analysis comprises an extraction of movement patterns of the user, a correlation between the medical data and the movement patterns of the user, a clustering of the user with other users associated with similar movement patterns and with other users associated with similar medical data, first correlations of the user and the other users sharing similar medical data with similar movement patterns and second correlations of the user and the other users sharing similar movement patterns with similar medical data.

2. The method according to claim 1, further comprising executing one or more of time-stamped beacon signaling, time-stamped cellular telephone service, time-stamped short messaging service (SMS) or time-stamped email service by the mobile device.

3. The method according to claim 1, wherein the mobile device comprises one or more of a smartphone, a tablet, a laptop or computerized fitness apparel.

4. The method according to claim 1, wherein the first and second data each comprises location and temporal data.

* * * * *